(12) United States Patent
Sung et al.

(10) Patent No.: US 8,236,940 B2
(45) Date of Patent: Aug. 7, 2012

(54) CONSTITUTIVE STRONG PROMOTER AND USE THEREOF

(75) Inventors: Moon Hee Sung, Daejeon (KR); Chul Joong Kim, Daejeon (KR); Seung-Pyo Hong, Daejeon (KR); Haryoung Poo, Daejeon (KR); Il Han Lee, Gyeonggi-do (KR); Ji Yeon Kim, Seoul (KR); Kwang Kim, Daejeon (KR)

(73) Assignees: Bioleaders Corporation, Daejeon (KR); Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/532,605

(22) PCT Filed: Mar. 21, 2008

(86) PCT No.: PCT/KR2008/001579
§ 371 (c)(1),
(2), (4) Date: Mar. 29, 2010

(87) PCT Pub. No.: WO2008/115019
PCT Pub. Date: Sep. 25, 2008

(65) Prior Publication Data
US 2010/0196956 A1     Aug. 5, 2010

(30) Foreign Application Priority Data
Mar. 22, 2007    (KR) .................... 10-2007-0027947

(51) Int. Cl.
*C07H 21/04*     (2006.01)
*C12N 15/63*     (2006.01)
*C12N 1/21*     (2006.01)
*C12P 21/00*     (2006.01)

(52) U.S. Cl. ................ 536/24.1; 435/320.1; 435/252.1; 435/71.1

(58) Field of Classification Search .................... None
See application file for complete search history.

(56) References Cited

FOREIGN PATENT DOCUMENTS
KR    10-0469800     4/2004
KR    10-2006-0088995    3/2007

OTHER PUBLICATIONS

EB433768, a *Nicotiana tabacum* cDNA clone, 2006.*
DN905713, Root *Solanum tuberosum* cDNA clone, 2005.*
van der Vossen et al., Appl. Environ. Microbiol., 53:2452, 1987.
Koivula et al., Appl. Environ. Microbiol., 57:333, 1991.
Ruyter et al., Appl. Environ. Microbiol., 62:3662, 1996.
Slos et al., Appl. Environ. Microbiol., 57:1333, 1991.
Seegers, Trends Biotechnol., 20:508, 2002.
Aires et al., Appl. Environ. Microbiol., 72:745, 2006.
Steidler et al., Nat. Biotechnol., 21:785, 2003.

* cited by examiner

*Primary Examiner* — Celine Qian
(74) *Attorney, Agent, or Firm* — Rabin & Berdo, PC

(57) ABSTRACT

Disclosed herein are an aldolase gene promoter and the use thereof, more particularly, disclosed are a promoter of aldolase gene derived from *Lactobacillus casei*, having a base sequence of SEQ ID NO: 1, an expression vector containing said promoter, and a recombinant microorganism transformed with said expression vector. The recombinant microorganism transformed with the expression vector containing the disclosed promoter can effectively express a target protein on the surface thereof, and thus will be useful as vaccine vehicles and the like.

24 Claims, 3 Drawing Sheets

CONSTITUTIVE STRONG PROMOTER AND USE THEREOF

CROSS-REFERENCES TO RELATED APPLICATIONS

This application is a U.S. national phase application, pursuant to 35 U.S.C. §371, of PCT/KR2008/001579, filed Mar. 21, 2008, designating the United States, which claims priority to Korean Application No. 10-2007-0027947, filed Mar. 22, 2007. The entire contents of the aforementioned patent applications are incorporated herein by this reference.

TECHNICAL FIELD

The present invention relates to an aldolase gene promoter derived from *Lactobacillus casei* and the use thereof, and more particularly to a promoter of aldolase gene derived from *Lactobacillus casei* represented by SEQ ID NO: 1, an expression vector containing said promoter, and a recombinant microorganism transformed with said expression vector.

BACKGROUND ART

Lactic acid bacteria, which are the most important microorganisms among food microorganisms, have acquired the GRAS (generally recognized as safe) status, and thus have been used in various foods. These lactic acid bacteria have plasmids, bacteriophages, transposons and the like, thus making it possible to develop vectors for introducing genes therein. Also, these lactic acid bacteria are easily transformed according to conventional methods known in the art, and are considered to be most suitable for edible purposes, because edible selectable marker genes have been established. In addition, lactic acid bacteria have the effects of inhibiting harmful intestinal bacteria, cleaning intestines, lowering blood cholesterol levels, increasing the nutritional value, inhibiting infection with pathogens and alleviating liver cirrhosis, as well as an anticancer effect and the effect of boosting the immune system through macrophage activation.

In order to produce useful heterologous proteins in lactic acid bacteria, highly efficient promoters (van der Vossen et al., *Appl. Environ. Microbiol.*, 53:2452, 1987; Koivula et al., *Appl. Environ. Microbiol.*, 57:333, 1991; Pascalle et al., *Appl. Environ. Microbiol.*, 62:3662, 1996) are required, but studies on the genomes of lactic acid bacteria are still very insufficient. Among the genomes of lactic acid bacteria, only constitutive the genomes of *Bifidobacterium longum* NCC 2705, *Enterococcus faecalis* V583 and *Lactobacillus plantarum* WFCS 1 have been sequenced to date, and studies on the genome sequencing of a variety of lactic acid bacteria are currently in progress. In addition, as promoters isolated from lactic acid bacteria, only promoters derived from the genomes of *Streptococcus thermophilus* A054, *Lactococcus lactis* MG1614 and *Lactococcus cremoris* Wg2 (Slos et al., *Appl. Environ. Microbiol.*, 57:1333,1991; Koivula et al., *Appl. Environ. Microbiol.*, 57:333, 1991; van der Vossen et al., *Appl. Environ. Microbiol.*, 53:2452, 1987)_are known to date.

Recently, in USA and Europe, studies on the development of live vaccines using lactic acid bacteria, studies on vehicles for delivering useful hormone drugs into the intestines, and studies on the establishment of efficient genetic resources therefor and the development of insertion vectors for lactic acid bacteria, are being conducted. Particularly, the utility of lactic acid bacteria as vaccine vehicles has been highly evaluated, because unmethylated CpG DNA, lipoteichoic acid, peptidoglycan and the like, which are contained in lactic acid bacteria in large amounts, are known to function as adjuvants. In addition, lactic acid bacteria have many advantages in that they can induce intestinal mucosal immunity, because they show resistance to bile acid and gastric acid to make it possible to deliver antigens to the intestines (Seegers, *Trends Biotechnol.*, 20:508, 2002).

However, in order for lactic acid bacteria to be used as vaccine vehicles, it is required to develop a technology of presenting antigen proteins for the production of disease-preventing antibodies to the inside or outside of bacterial cells so as to allow antigen-antibody reactions to occur smoothly. In fact, various study results, which indicate that lactic acid bacteria are suitable as vaccine vehicles, have been published. Examples of these studies include the examination of the antibody-inducing capacity of lactic acid bacteria, in which the L1 protein of human papilloma virus (HPV) is expressed (Aires et al., *Appl. Environ. Microbiol.*, 72:745, 2006), and the examination of the disease-treating effects of a lactic acid bacterial strain which secrets and expresses IL-2 (interleukin-2) (Steidler et al., *Nat. Biotechnol.*, 21:785, 2003).

As described above, the development of various applications of lactic acid bacteria expressing target proteins, and scientific studies on the lactic acid bacteria, have been actively conducted, there are problems in that the expression levels of the target proteins are insufficient and that, when inducible promoters are used, the continued expression of the target proteins in vivo can also be impossible.

Previously, the present inventors developed a novel vector for effectively expressing exogenous protein on the surface of microorganisms, using a poly-gamma-glutamic acid synthetase complex A (pgsBCA) gene, derived from *Bacillus subtilis* var. Chungkookjang, as a novel surface anchoring motif, and a method for expressing a large amount of target proteins on the surface of microorganisms transformed with said vector (Korean Patent Registration No. 10-0469800).

Accordingly, the present inventors have understood that, if a vector capable of stably expressing an antigen or an antigen determinant at a high level in lactic acid bacteria using the surface anchoring motif described in said patent is developed, it will be possible to develop a vaccine, which is compatible with the human body and can efficiently induce an immune response, because the antigen is exposed on the surface of lactic acid bacteria. Based on this understanding, the present inventors have conducted a process of screening a promoter capable of highly expressing a target protein in lactic acid bacteria and, as a result, have found that, when an aldolase gene promoter is used, the expression of target genes is increased by at least 2.5 times compared to when a conventional promoter is used, thereby completing the present invention.

SUMMARY OF INVENTION

It is a main object of the present invention to provide a promoter of aldolase gene derived from *Lactobacillus casei*, which induces an increase in the expression of target genes.

Another object of the present invention is to provide an expression vector, in which said promoter and a gene encoding a target protein are linked to each other.

Still another object of the present invention is to provide a recombinant microorganism transformed with said expression vector, and a method for preparing a target protein using said recombinant microorganism.

Yet another object of the present invention is to provide a method for preparing a microbial vaccine using said recombinant microorganism.

To achieve the above objects, in one aspect, the present invention provides a promoter of aldolase gene derived from *Lactobacillus casei*, which induces an increase in the expression of target genes.

In another aspect, the present invention provides an expression vector, in which a target gene is linked to the terminus of said promoter, and a recombinant microorganism transformed with said expression vector.

In still another aspect, the present invention provides a microbial surface expression vector, in which said promoter, a poly-gamma glutamic acid synthetase complex gene and a gene encoding a target protein are linked to each other, and a recombinant microorganism transformed with said microbial surface expression vector.

In still another aspect, the present invention provides a method for expressing a target protein on the surface of a microorganism, the method comprising culturing said recombinant microorganism.

In still another aspect, the present invention provides a method for preparing a microbial vaccine, the method comprising culturing the recombinant microorganism transformed with said surface expression vector.

Other features and aspects of the present invention will be apparent from the following detailed description and the appended claims.

DETAILED DESCRIPTION EMBODIMENTS

Figure 1:
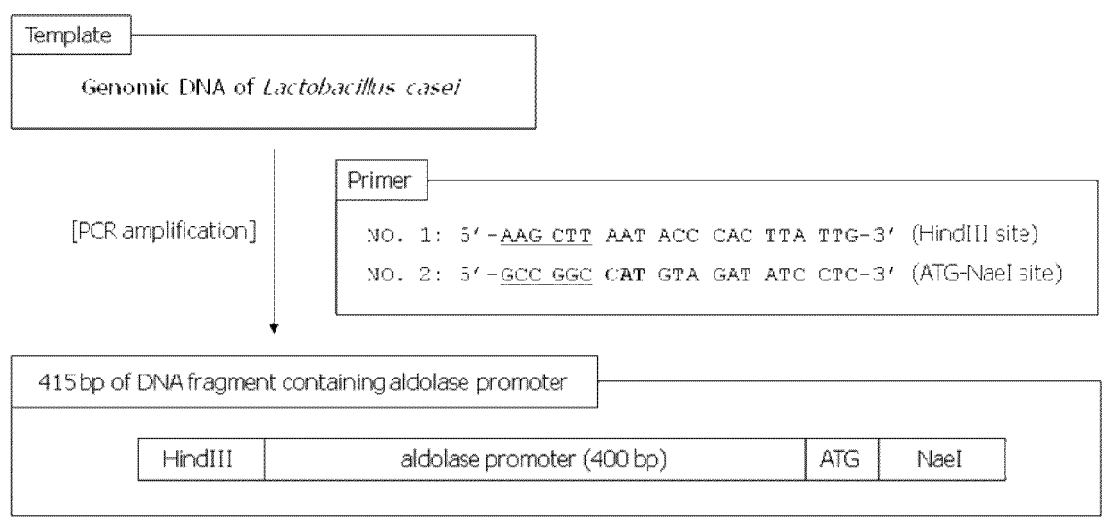
FIG. 1 shows a method of obtaining an aldolase gene promoter from the genomic DNA of *Lactobacillus casei*.

In one aspect, the present invention relates to a promoter of aldolase gene derived from *Lactobacillus casei*.

In the present invention, in order to construct an aldolase gene promoter, a *Lactobacillus casei*-derived aldolase gene promoter was amplified by PCR, and a 400-bp promoter (SEQ ID NO: 1) derived from *Lactobacillus casei* was isolated using a gene cloning technique. The aldolase gene promoter of the present invention is a promoter inducing the expression of aldolase gene present in *Lactobacillus casei*. Generally, promoters include a region to which RNA polymerase binds to induce the initiation of transcription, and the degree of RNA synthesis is determined depending on the base sequences of promoters. For this reason, the expression level of a gene can vary depending on the kind of promoter.

In order to measure the expression inducion capacity of the promoter of the present invention, an alpha-amylase gene was inserted into each of an expression vector containing said promoter and an expression vector containing an ldh or slpA promoter, and the constructed vectors were used to transform *Lactobacillus casei*. Then, the enzyme activity of amylase, the expression of which has been induced by each of the promoters, was measured. As a result, the amylase enzyme activity was shown to be the highest in transformants containing the aldolase gene promoter. This suggests that the expression-inducing activity of the promoter of the present invention was stronger than those of the two conventional promoters.

In another aspect, the present invention relates to an expression vector containing the aldolase gene promoter and a gene encoding target protein; and a recombinant microorganism transformed with said expression vector.

An expression vector minimally requires a promoter enabling transcription, a gene expressing a target protein downstream of the promoter, a gene which can be amplified by self-replication in microorganisms, and an antibiotic selection marker gene for selecting a target vector, and said genes except for the target gene can vary depending on the backbone of the vector and a selected host cell. The genes minimally required in vector construction are widely known to those skilled in the art and can be easily selected depending on the expression conditions and intended use of a target gene. Generally, the backbone of the vector may have a replication origin of pWV01 or pAMβ1, but the scope of the present invention is not limited thereto.

Various methods and means may be used to introduce a vector or DNA sequence for expressing not only a target protein, but also a gene containing a regulatory region, into an appropriate host cell. For example, biochemical methods, such as transformation, transfection, conjugation, protoplast fusion and calcium phosphate precipitation, or physical methods, DEAE (diethylaminoethyl) dextran and electroporation, may be used.

After the expression vector is introduced into an appropriate host cell, only transformants can be screened using conventional techniques known in the art. In other words, transformants containing the vector capable of expressing a target gene can be screened using a selection medium suitable for the growth of host cells containing antibiotic substances.

As used herein, the term "target protein" or "heterologous protein" means a protein which is not normally present in the transformed host cells expressing the protein. For example, when a virus-derived or tumor-derived protein is manipulated to be artificially expressed in lactic acid bacteria, the protein will be referred to as "heterologous protein" or "target protein".

In still another aspect, the present invention relates to a surface expression vector for microorganisms, which has the aldolase gene promoter, a poly-gamma glutamic acid synthetase complex gene and a gene encoding a target protein linked to each other, and a recombinant microorganism transformed with said microbial surface expression vector.

The downstream of the promoter contains a poly-gamma glutamic acid synthetase complex gene, which is a surface expression motif, located between the promoter and the target protein in the DNA sequence of the vector. The gene of the surface anchoring motif plays a decisive role in the surface expression of the target gene, because it is linked to the initial portion of the target protein so as to induce the expressed protein to bind to lipid of the cell membrane, after it is encoded into amino acids. A method of linking the gene of the surface anchoring motif with the promoter and the target gene can be performed by conventional techniques which can be easily practiced by those skilled in the art, including PCR, restriction enzyme digestion and ligation.

The target proteins, which are expressed by the promoter of the present invention and displayed on the surface of host cells, may be enzymes, antibodies, antigens, adsorption proteins or adhesion proteins, and preferably antigens.

Said target proteins or antigens may include, but are not limited to, infectious microorganisms, immune disease-derived antigens or tumor-derived antigens, for example, fungal pathogens, bacteria, parasites, helminths, viruses or allergy-causing substances. More specifically, the antigens include tetanus toxoid, hemagglutinin molecules or nuclera protein of influenza virus, diphtheria toxoid, HIV gp120 or its fragments, HIV gag protein, IgA protease, insulin peptide B, *Spongospora* subterranea antigen, vibriose antigens, *Salmonella* antigens, pneumococcus antigens, respiratory syncytial virus antigens, *Haemophilus influenza* outer membrane protein, *Streptococcus pneumoniae* antigen, *Helicobacter pylori* urease, *Neisseria meningitidis* pilins, *N. gonorrhoeae* pilins, melanoma-associated antigens (TRP-2, MAGE-1, MAGE-3, gp-100, tyrosinase, MART-1, HSP-70, beta-HCG), human papilloma virus antigens E1, E2, E6 and E7 derived from HPV type 16, 18, 31, 33, 35 or 45, tumor antigen CEA, normal or mutant ras protein, normal or mutant p53 protein, Muc1, pSA, antigens well known in the art, which is derived from the followings: cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, Addison's disease, immunogens, allergen, cancer including solid and blood borne tumors, acquired immune deficiency syndrome, and factor involved in transplant rejection, such as kidney, heart, pancreas, lung, bone, and liver transplant rejections, and antigens inducing autoimmunity.

As used herein, the term "host cells" or "microorganisms" means probiotic gram-positive lactic acid bacteria. Common criteria used for selecting probiotic microorganisms include: (i) microorganisms of human origin; (ii) being stable in bile, acid, enzyme and oxygen; (iii) capability to adhere to the intestinal mucosal membrane; (iv) capability to form colonies in the digestive organs; (v) capability to produce antibacterial substances; and (vi) unequivocal demonstration of efficacy or stability. Based on the above conditions, it is evident that lactic acid bacteria are biocompatible and harmless to the human body during the growth thereof in the human body. Thus, when transformants containing lactic acid bacteria as hosts are applied to the human body so as to deliver genes or proteins for preventing or treating diseases, a step of detoxifying bacterial strains is not required, unlike conventional methods of preparing vaccines using bacterial strains.

In the present invention, the microorganisms may include *Lactobacillus* sp., *Streptococcus* sp. and *Bifidobacterium* sp. Typically, *Lactobacillus* sp. includes *L. acidophilus, L. casei, L. plantarum, L. ferementum, L. delbrueckii, L. johnsonii* LJI, *L. reuteri* and *L. bulgaricus; Streptococcus* sp. includes *S. thermophilus*; and *Bifidobacterium* sp. includes *B. infantis, B. bifidum, B. longum, B. psuedolongum, B. breve, B. lactis* Bb-12 and *B. adolescentis*. Preferred is *Lactobacillus* sp.

In the present invention, an expression vector (pDT1-PgsAL-Amylase), which contains a base sequence having the promoter linked to a surface anchoring motif pgsA and can express an alpha-amylase gene as a target gene, was constructed, and the expression vector was inserted into *L. casei*, thus preparing transformants expressing amylase.

The target protein, which is expressed by the inventive promoter having improved gene expression capacity, is expressed on the surface of microorganisms, and thus the transformed microorganisms of the present invention can be used as vaccines.

In still another aspect, the present invention relates to a method for preparing a microbial vaccine, the method comprising culturing the recombinant microorganism transformed with said surface expression vector.

Vaccines are drugs which are used to stimulate the immune system using bio-organisms in order to prevent diseases. As used herein, the term "immune activation" means a process of efficiently removing an antigen by the production of antibodies in organisms, stimulation of T-lymphocytes or the stimulation of other immune cells (e.g. macrophages). An introduction to immunology of the immune activation will be readily understood by those skilled in the art (Barrett, J. T., *Textbook of Immunology*, 1983).

The vaccine comprising a transformed microorganism, which expresses an antigen, may be administered to mammals, and preferably human beings.

The preparation of the vaccine composition can be carried out using a standard technique, and the amount required will vary with the antigenicity of the gene product and need only be an amount sufficient to induce an immune response typical of existing vaccines. Routine experimentation will easily establish the required amount. Typical initial dosages of vaccine could be 0.001-1 mg antigen/kg body weight, with increasing amounts or multiple dosages used as needed to provide the desired level of protection. The required amount can be determined by those skilled in the art and may vary depending on various factors, such as formulation method, administration mode, age, weight and sex of patients, pathological conditions, diet, administration time, administration route, excretion rate and response sensitivity.

In order for a vaccine to be effective in producing antibodies, the antigenic material must be released in such a way that the antibody-producing mechanism of the vaccinated animal can come into play. Therefore, the microbe carrier of the gene product must be introduced into the body. In order to stimulate a preferred response by an antigen presented by the transformants of the present invention, introduction of the microbe or gene product directly into the gut or bronchus is preferred, such as by oral administration, gastric intubation or intranasally in the form of aerosols, although other methods of administering the vaccine, such as intravenous, intramuscular or subcutaneous injection, are possible.

The vaccine is advantageously presented in a lyophilized form, for example in a capsular form, for oral administration to a patient. Such capsules may be provided with an enteric coating comprising for example Eudragate S, Eudragate L, cellulose acetate, cellulose phthalate or hydroxy propylmethyl cellulose. These capsules may be used as such, or alternatively, the lyophilised material may be reconstituted prior to administration, e.g. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively the vaccine may be prepared for parenteral administration, intranasal administration or intramammary administration.

The transformed lactic acid bacteria, which include the inventive promoter and contain a gene expressing a target protein capable of acting as an antigen, can show the desired efficacy while forming colonies in mucosa in the digestive organs, can be simultaneously administered together with selective antibiotics in the vector for active colony formation while maintaining the desired transformation properties, and can control the development of undesired lactic acid bacteria having no vector, which can be developed during cell division in transformants. The selection method can be easily performed using conventional techniques known in the art, and the selective antibiotics, which can be used in the above process, may vary depending on antibiotic genes contained in the expression vector.

EXAMPLES

Hereinafter, the present invention will be described in further detail with reference to examples. It is to be understood, however, that these examples are for illustrative purposes only and are not to be construed to limit the scope of the present invention.

Particularly, although only an amylase gene was exemplified as a target gene in the following examples, those skilled in the art will appreciate that the scope of the present invention is not limited thereto.

Example 1

Construction of *Lactobacillus casei*-Derived Aldolase Gene Promoter

A 400-bp DNA fragment corresponding to the promoter region of the aldolase gene was obtained by PCR from *Lactobacillus casei* ATCC 393.

For this purpose, *Lactobacillus casei* was cultured in basal MRS medium (containing 1% casein hydrolysate, 1.5% yeast extract, 2% dextrose, 0.2% ammonium citrate, 0.5% sodium acetate, 0.01% magnesium sulfate, 0.05% manganese sulfate and 0.2% dipotassium phosphate; Acumedia Manufacturers, Inc.), and $10^9$ cultured cells were disrupted to obtain a solution. The solution was used as a template for PCR. In order to facilitate insertion into a vector in gene cloning, HindIII and NaeI restriction sites were located at the ends of each of primers (SEQ ID NO: 2 and SEQ ID NO: 3). PCR was performed using the primers and, as a result, an amplified product (SEQ ID NO: 1) having a total length of 415 bp was obtained. The PCR-amplified product was cloned into a pGEM-Teasy vector (Promega Co., USA), and the base sequence thereof was analyzed (FIG. 1).

```
SEQ ID NO: 2:
5'-aag ctt aat acc cac tta ttg-3'

SEQ ID NO: 3:
5'-gcc ggc cat gta gat atc ctc-3'
```

Example 2

Construction of Amylase Surface Expression Vector Using Aldolase Gene Promoter

Figure 2:
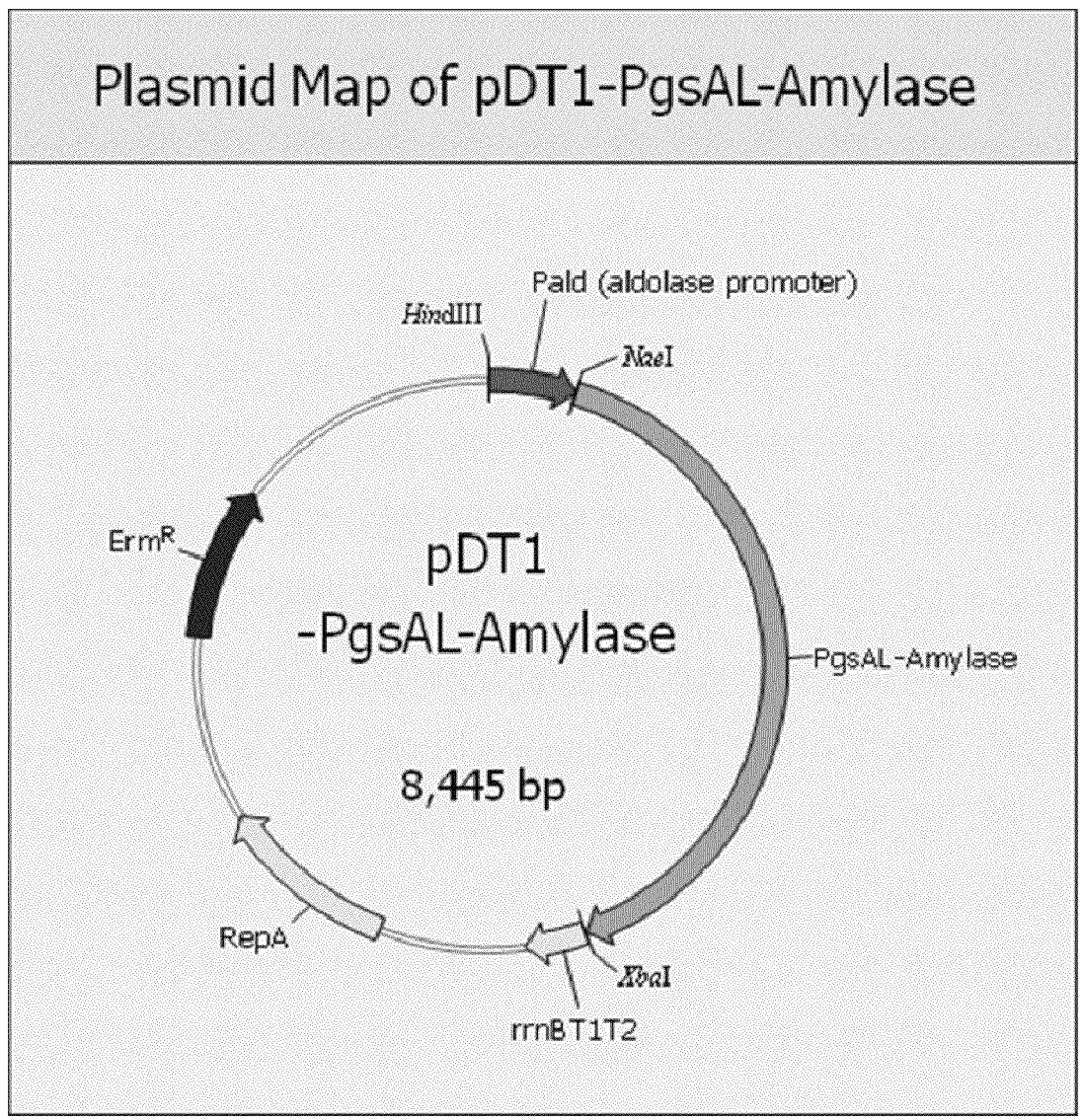
FIG. 2 is a map of a vector for expressing amylase on the surface of lactic acid bacteria, in which the vector is constructed using the aldolase gene promoter.

In order to prepare an amylase expression vector whose expression is induced by an aldolase gene promoter, the *Lactobacillus casei*-derived aldolase gene promoter was inserted into a vector having RepA, as a replication origin, which is replicable in *E. coli* and *Lactobacillus casei*, and then a surface anchoring motif pgsA derived from *Bacillus subtilis* var. Chungkookjang was introduced downstream of the promoter, and BamHI and XbaI restriction enzyme sites, allowing a target gene to be inserted into the carboxy end of the pgsA gene, was added thereto, thus constructing a pDT1-PgsA vector containing the aldolase gene promoter. As the pgsA gene, the one disclosed in Korean Patent 0469800 was used. Also, as a selection marker for maintaining the vector, an erythromycin-resistant gene was selected (FIG. 2).

In order to obtain an α-amylase gene, PCR was performed using Streptococcus bovis (ATCC 700410)-derived genome as a template with primers of SEQ ID NO: 4 and SEQ ID NO: 5.

```
SEQ ID NO: 4:
5'-tct gga tcc gat gaa caa gtg tca atg-3'
```

```
SEQ ID NO: 5:
5'-cag tta tct aga tta ttt tag ccc atc-3'
```

As a result, a 2,130-bp DNA gene fragment, which had a sequence encoding 703 amino acids except for 39 N-terminal amino acid residues, as the secretion signal of extracellular α-amylase, and contained BamHI and XbaI restriction enzyme sites at both ends, respectively, was obtained.

The DNA fragment containing the a-amylase gene was transformed into lactic acid bacterial host cells by digesting the DNA fragment with BamHI and XbaI and ligating the digested fragment into the C terminal end of PgsA of the pJT1-PgsA vector. As a result, an expression vector pDT1-PgsA-amylase, which could express a PgsA-α-amylase fusion protein on the surface of bacterial cells, was constructed (FIG. 2).

Example 3

Preparation of Transformants Using Alpha-Amylase Surface Expression Vector

*Lactobacillus casei* was transformed with an alpha-amylase surface expression vector pDT1-PgsA-amylase, and PCR was performed in the following manner in order to examine whether the alpha-amylase gene-containing vector would be present in the transformant. The transformed strain was recovered and washed with water, and PCR was performed using the washed strain as a template with primers (SEQ ID NO: 6 and SEQ ID NO: 7) which were annealed in the erythromycin-resistant gene contained in the plasmid. Thus, it was confirmed by detecting a 1,156-bp PCR product, indicating that the target vector was present in the transformant.

```
SEQ ID NO: 6:
5'-gtg tgt tga tag tgc agt atc-3'
```

```
SEQ ID NO: 7:
5'-ccg tag gcg cta ggg acc tct tta gc-3'
```

In addition, in order to analyze whether the gene was normally expressed in the vector inserted into the transformant, the measurement of alpha-amylase enzyme activity was carried out as described in Example 4.

Example 4

Comparison of Promoter Activities Through Measurement of Amylase Activity

The expression-inducing activity of the novel aldolase gene promoter was compared with those of the existing ldh promoter and slpA promoter. An amylase gene as a reporter gene was linked to each of the promoters, and the expression-inducing activities of the promoters were compared through the measurement of amylase enzyme activity proportional to the expression level of amylase.

The existing vectors used to compare the promoter activities were pJT1-PgsAL-Amylase (Korean Patent 0578395) expressing amylase using the ldh promoter, and pBT-PgsAL-Amylase (Korean Patent Application No. 10-2006-0088995) expressing amylase using the slpA promoter. The two vectors have the same structure as that of pDT1-PgsAL-Amylase, but are different from each other with respect to the promoter region.

The enzyme activity of amylase expressed on the surface of the lactic acid bacteria was measured using an Enzyme-Activity Assay Kit (Kikkoman Co., Tokyo, Japan) and N3-G5-β-CNP (2-chloro-4-nitrophenyl 6⁵-azido-6⁵-deoxy-β-maltopentaoside) as a substrate.

The bacterial cells recovered by centrifuging culture broth were washed twice with PBS solution and suspended in 100 μl of the same buffer solution. The cell suspension was mixed with 400 μl of a substrate solution, and the mixture was incubated at 37° C. for 10 minutes to induce an enzymatic reaction. 800 μl of a reaction stop solution was added thereto to stop the reaction, and the absorbance at 400 nm was measured with a spectrophotometer. 1 unit of enzyme was defined as the amount of enzyme that produces 1 μmole of CNP (2-chloro-4-nitrophenol) showing absorbance at 400 nm, from N3-G5-β-CNP at 37° C. for 1 minute.

To culture Lactobacillus casei transformed with each of the vectors, MRS medium containing erythromycin (SIGMA-ALDRICH Co.) at a final concentration of 16 μg/ml was used, and the culture process was performed in a 3-L fermenter containing 2.0 L of the medium. Culture broth was recovered at 4-hr intervals starting 5 hours after the initiation of the culture process and was measured for the number of living bacteria and amylase activity. For pH adjustment in the culture process, NaOH was used.

Figure 3:
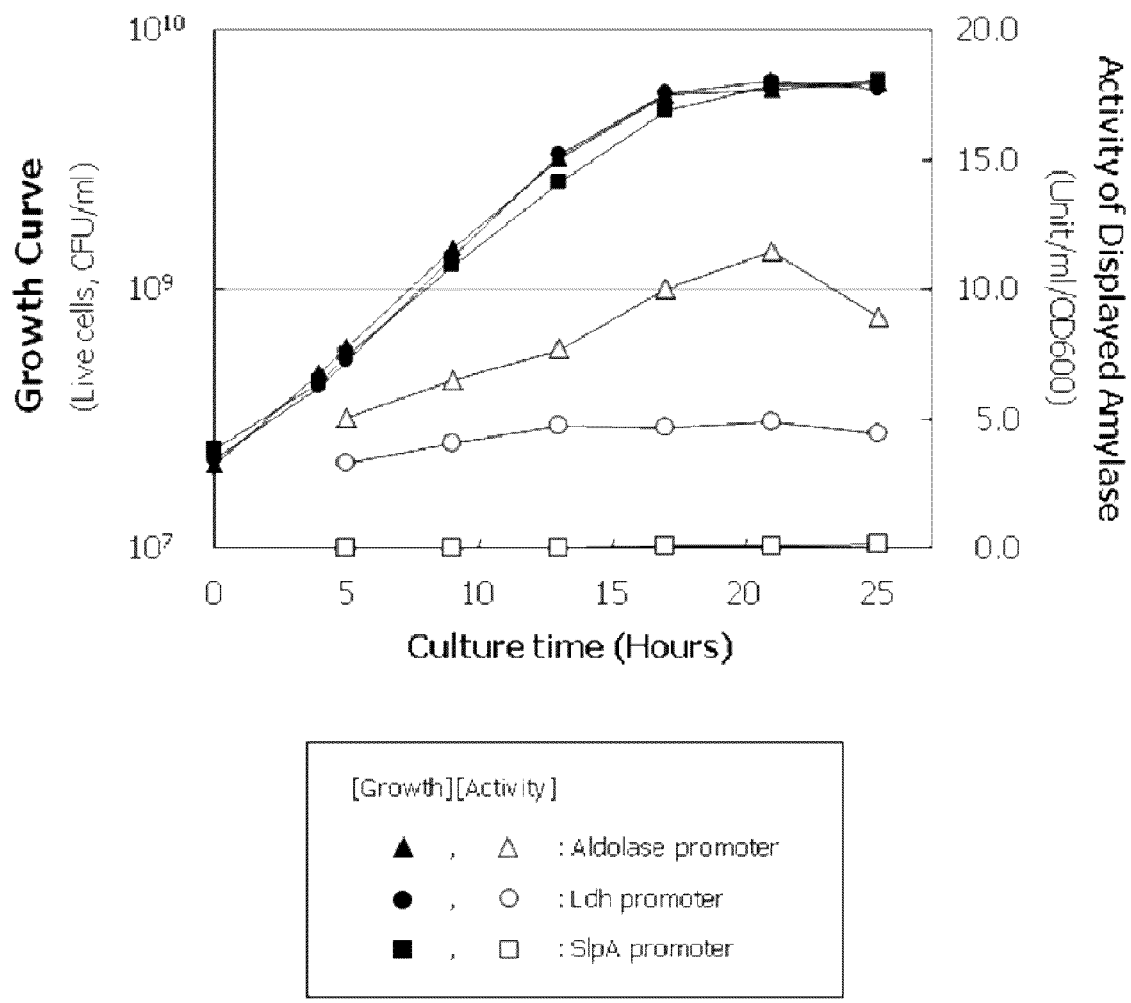
FIG. 3 shows comparison of gene expression activities between promoters during the growth period of the lactic acid bacteria, in which the gene expression activities were determined through the measurement of amylase enzyme activity (unit/ml/OD600).

As a result, it could be observed that the use of the aldolase gene promoter showed amylase activity, which was 2.0-2.5 fold higher than that of the ldh promoter and 150 to 180 fold higher than that of the slpA promoter. This suggests that the activity of the aldolase gene promoter was stronger than those of the ldh and slpA promoters (FIG. 3).

INDUSTRIAL APPLICABILITY

As described in detail above, the present invention provides a Lactobacillus casei-derived aldolase promoter, which can highly express a target protein in lactic acid bacteria, and an expression vector containing said promoter. Because the vector contains a gene expressing a target protein on the surface of microorganisms, lactic acid bacteria transformed with the vector can effectively express a target protein on the surface thereof, and thus the transformed lactic acid bacteria can be used as vaccine vehicles.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A promoter of a *Lactobacillus casei* aldolase gene.

2. The promoter according to claim 1, which has a base sequence of SEQ ID NO: 1.

3. An expression vector, which contains the promoter of claim 1 and a gene encoding a target protein.

4. A recombinant microorganism transformed with the expression vector of claim 3.

5. A microbial surface expression vector, which has the promoter of claim 1, a poly-gamma glutamic acid synthetase complex gene, and a gene encoding a target protein linked to each other.

6. The microbial surface expression vector according to claim 5, wherein the target protein is an antigen.

7. The microbial surface expression vector according to claim 5, wherein the poly-gamma glutamic acid synthetase complex gene is pgsA.

8. A recombinant microorganism transformed with the microbial surface expression vector of claim 5.

9. The recombinant microorganism according to claim 8, wherein said microorganism is a lactic acid bacterium.

10. A method for expressing a target protein on the surface of a microorganism, the method comprises culturing the recombinant microorganism of claim 8.

11. A method for preparing a microbial vaccine, the method comprising: expressing an antigen on the surface of a microorganism by culturing the recombinant microorganism transformed with the microbial surface expression vector of claim 6; and recovering the microorganism having said antigen expressed on the surface thereof.

12. The method for preparing a microbial vaccine according to claim 11, wherein said microorganism is a lactic acid bacterium.

13. A recombinant microorganism transformed with the microbial surface expression vector of claim 6.

14. A recombinant microorganism transformed with the microbial surface expression vector of claim 7.

15. An expression vector, which contains the promoter of claim 2 and a gene encoding a target protein.

16. A recombinant microorganism transformed with the expression vector of claim 15.

17. A microbial surface expression vector, which has the promoter of claim 2, a poly-gamma glutamic acid synthetase complex gene, and a gene encoding a target protein linked to each other.

18. The microbial surface expression vector according to claim 17, wherein the target protein is an antigen.

19. The microbial surface expression vector according to claim 17, wherein the poly-gamma glutamic acid synthetase complex gene is pgsA.

20. A recombinant microorganism transformed with the microbial surface expression vector of claim 17.

21. The recombinant microorganism according to claim 20, wherein said microorganism is a lactic acid bacterium.

22. A method for expressing a target protein on the surface of a microorganism, the method comprising culturing the recombinant microorganism of claim 20.

23. A recombinant microorganism transformed with the microbial surface expression vector of claim 18.

24. A recombinant microorganism transformed with the microbial surface expression vector of claim 19.

* * * * *

SEQUENCE LISTING

```
<160> NUMBER OF SEQ ID NOS: 7

<210> SEQ ID NO 1
<211> LENGTH: 415
<212> TYPE: DNA
<213> ORGANISM: Lactobacillus casei

<400> SEQUENCE: 1
aagcttaata cccacttatt gcgatttgct tttctattag ttagcatttt aaattgtgaa      60
acgtgccact tataaacaaa tttccgtctt cttttttatga gagtaatctc atttaatctt    120
gactaaatat ccgattgcgg tcacacaact accagtttca aacaaatttc aatttgatgg    180 tcattttta ttttgtcggc aaaaagtgag caaatcagta gcattttccc tgattacggg     240
gtacattcaa agtgactttg cgtacacaca gacatatgta tgacgggtgt tataaaaagc    300
cgtcacgctg ctcgagtagc tctcatcatt ttctcgccct tttctcccgc aacatatgat    360
aaaatacaac ggttgtgaat tgtttatttc ctaggaggat atctacatgg ccggc         415

<210> SEQ ID NO 2
<211> LENGTH: 21
<212> TYPE: DNA
<213> ORGANISM: Artificial
<220> FEATURE:
<223> OTHER INFORMATION: Forward primer

<400> SEQUENCE: 2
aagcttaata cccacttatt g                                                21

<210> SEQ ID NO 3
<211> LENGTH: 21
<212> TYPE: DNA
<213> ORGANISM: Artificial
<220> FEATURE:
<223> OTHER INFORMATION: Reverse Primer

<400> SEQUENCE: 3
```

-continued

```
gccggccatg tagatatcct c                                          21

<210> SEQ ID NO 4
<211> LENGTH: 27
<212> TYPE: DNA
<213> ORGANISM: Artificial
<220> FEATURE:
<223> OTHER INFORMATION: Forward Primer

<400> SEQUENCE: 4
tctggatccg atgaacaagt gtcaatg                                    27

<210> SEQ ID NO 5
<211> LENGTH: 27
<212> TYPE: DNA
<213> ORGANISM: Artificial
<220> FEATURE:
<223> OTHER INFORMATION: Reverse Primer

<400> SEQUENCE: 5
cagttatcta gattatttta gcccatc                                    27

<210> SEQ ID NO 6
<211> LENGTH: 21
<212> TYPE: DNA
<213> ORGANISM: Artificial
<220> FEATURE:
<223> OTHER INFORMATION: Forward Primer

<400> SEQUENCE: 6
gtgtgttgat agtgcagtat c                                          21

<210> SEQ ID NO 7
<211> LENGTH: 26
<212> TYPE: DNA
<213> ORGANISM: Artificial
<220> FEATURE:
<223> OTHER INFORMATION: Reverse Primer

<400> SEQUENCE: 7
ccgtaggcgc tagggacctc tttagc                                     26
```